(12) United States Patent
Kaminski et al.

(10) Patent No.: US 10,451,567 B2
(45) Date of Patent: Oct. 22, 2019

(54) RADIOGRAPHIC PRODUCT INSPECTION SYSTEM WITH REJECT BIN

(71) Applicant: Mettler-Toledo, LLC, Columbus, OH (US)

(72) Inventors: Kamil Kaminski, Papworth Everard (GB); Ivana Nanut, Royston (GB)

(73) Assignee: Mettler-Toledo, LLC, Columbus, OH (US)

( * ) Notice: Subject to any disclaimer, the term of this patent is extended or adjusted under 35 U.S.C. 154(b) by 0 days.

(21) Appl. No.: 16/166,640

(22) Filed: Oct. 22, 2018

(65) Prior Publication Data

US 2019/0154599 A1  May 23, 2019

(30) Foreign Application Priority Data

Nov. 17, 2017 (EP) ..................... 17202287

(51) Int. Cl.
| | |
|---|---|
| *B65G 47/82* | (2006.01) |
| *G01N 23/083* | (2018.01) |
| *G01N 23/18* | (2018.01) |
| *B65G 47/46* | (2006.01) |
| *B07C 5/36* | (2006.01) |
| *B65G 43/00* | (2006.01) |
| *G01N 23/04* | (2018.01) |
| *G01N 33/00* | (2006.01) |

(52) U.S. Cl.
CPC ........... *G01N 23/083* (2013.01); *B07C 5/362* (2013.01); *B65G 43/00* (2013.01); *B65G 47/46* (2013.01); *B65G 47/82* (2013.01); *G01N 23/04* (2013.01); *G01N 23/18* (2013.01); *B65G 2201/0235* (2013.01); *B65G 2203/0208* (2013.01); *B65G 2203/042* (2013.01); *B65G 2207/30* (2013.01); *G01N 2033/0081* (2013.01)

(58) Field of Classification Search
CPC .... B65G 47/46; B65G 47/82; B65G 2207/30; B07C 5/362
USPC ...................... 198/367, 368, 860.4
See application file for complete search history.

(56) References Cited

U.S. PATENT DOCUMENTS

| | | | | |
|---|---|---|---|---|
| 3,899,915 A | * | 8/1975 | Williams, Jr. | G01G 11/006 73/1.13 |
| 5,735,387 A | * | 4/1998 | Polaniec | G01N 35/04 198/465.1 |
| 6,512,812 B2 | | 1/2003 | Watanabe | |

(Continued)

FOREIGN PATENT DOCUMENTS

JP  3867209 B2  10/2006

*Primary Examiner* — Joseph A Dillon, Jr.
(74) *Attorney, Agent, or Firm* — Standley Law Group LLP; Jeffrey S. Standley; Stephen L. Grant

(57) ABSTRACT

In an X-ray inspection system (1), a reject bin (14) is split into a reject bin top (15) and a reject bin bottom (16) along a separation gap (17) which is arranged at the level of a transport section (21) of a conveyor belt loop (10) and runs uninterrupted from the outfeed opening (26) to the conveyor access opening (43) which, in turn, continues uninterrupted to the infeed opening (8). After a conveyor access door (19) has been opened and a tensioning mechanism (32) has been released, the conveyor belt loop can be taken out of the enclosure cabinet (5) by sliding the transport section (21) through the separation gap and the conveyor access opening and simultaneously slipping a return section (22) of the conveyor belt loop around the reject bin bottom.

18 Claims, 3 Drawing Sheets

(56) References Cited

U.S. PATENT DOCUMENTS

| | | | |
|---|---|---|---|
| 6,578,697 B2 * | 6/2003 | Bonham | B65G 47/44 198/370.07 |
| 9,696,326 B2 | 7/2017 | Parmee | |
| 2002/0060174 A1 * | 5/2002 | Nakajima | B07C 5/362 209/644 |
| 2003/0034233 A1 * | 2/2003 | Lunghi | B65G 15/00 198/835 |
| 2005/0067254 A1 * | 3/2005 | Jones | B07C 5/362 198/370.07 |
| 2008/0047760 A1 * | 2/2008 | Georgitsis | G01G 19/40 177/1 |
| 2011/0048104 A1 * | 3/2011 | Parmee | G01N 21/274 73/1.79 |
| 2014/0091013 A1 * | 4/2014 | Streufert | B65G 47/46 209/552 |
| 2015/0052967 A1 * | 2/2015 | Parmee | G01N 35/00623 73/1.01 |
| 2015/0352596 A1 * | 12/2015 | Yamakawa | G01G 19/03 209/596 |
| 2017/0057751 A1 * | 3/2017 | Fujihara | B65G 47/22 |
| 2018/0250715 A1 * | 9/2018 | Suda | B07C 5/36 |
| 2018/0339381 A1 * | 11/2018 | Aoki | B23Q 7/06 |
| 2019/0126324 A1 * | 5/2019 | Ackley | B07C 5/3422 |

\* cited by examiner

RADIOGRAPHIC PRODUCT INSPECTION SYSTEM WITH REJECT BIN

CROSS-REFERENCE TO RELATED APPLICATIONS

This application claims priority to European Patent Application No. 17202287.3, filed on 17 Nov. 2017, which is incorporated by reference as if fully recited herein.

TECHNICAL FIELD

The invention relates to the field of in-line radiation inspection equipment, i.e. systems that are typically used for the inspection of articles in production and packaging lines.

BACKGROUND ART

Radiation scanner systems that are used to detect foreign objects and contaminants in food products and pharmaceutical products belong to the known state of the art. For the protection of personnel in the proximity of the equipment, the radiation in a scanner system of this type needs to be contained inside an enclosure cabinet which can be divided into an infeed compartment, a radiation inspection compartment, and an outfeed compartment. A belt conveyor which is normally part of the system and is arranged inside the enclosure cabinet carries the arriving articles through the infeed compartment, through the radiation inspection compartment, and through the outfeed compartment. In the radiation inspection compartment, an X-ray generator is arranged at some distance above the conveyor belt, while a radiation detector is arranged immediately underneath the top portion of the conveyor belt, i.e. vertically in between the forward moving section and the return section of the conveyor belt loop. Thus, an article travelling on the conveyor belt is traversed by the radiation from the radiation generator above the belt, and the rays transmitted by the article and the belt are received by the radiation detector below the top section of the belt.

Such a system normally includes or is operatively connected to a rejection mechanism which is arranged downstream of the radiation inspection compartment and serves to remove articles that were found to contain foreign objects or contaminants, so that the stream of articles continuing down the line contains only acceptable articles. The rejection mechanism causes the rejected articles to be moved off the conveyor belt into a reject bin where they are collected for further investigation, disposal or other special treatment.

The conveyor belt is typically made of a flexible polymer material. It must be easily accessible for cleaning as well as easy to uninstall and reinstall for maintenance and replacement. Since the belt is of a seamless closed-loop configuration, the requirement for easy uninstallation and reinstallation poses certain design challenges which have been addressed in known designs of the prior art.

For example in a conveyor belt arrangement proposed in JP 3867209 B2, only one end of each belt roller is supported by a bearing, so that the belt rollers can be compared to cantilever arms. After opening an enclosure door and loosening a belt-tensioning device, the belt can be pulled off the free end of the belt rollers. As an area of concern with this concept of cantilevered belt rollers, the transverse and friction forces in the bearings of the belt rollers would be bigger by an order of magnitude than they are in a conventional belt conveyor with bearings at both ends of each roller axle. This would necessitate the use of larger and stronger bearings which would have to be mounted in a commensurately solid and massive one-sided supporting structure of the conveyor belt.

In another arrangement which is described in U.S. Pat. No. 6,512,812 B2, the conveyor bed with the X-ray detector is configured as an integral X-ray detection unit, i.e. a subassembly within the enclosure cabinet, which can be taken out for cleaning, maintenance or belt exchange.

The applicant of the present invention manufactures radiation inspection systems wherein both the infeed compartment and the outfeed compartment are configured analogous to the air locks that are used for clean rooms. The entrance into the infeed compartment, the interior passages from the infeed compartment to the radiation inspection compartment and from the radiation inspection compartment to the outfeed compartment, as well as the exit from the outfeed compartment are protected by shielding curtains. Such shielding curtains are commonly configured as vertically slit sheets of rubber or of a rubber-like material containing a radiation-blocking component such as lead oxide or tungsten, for example as a sandwiched laminate or in distributed form. An entire shielding curtain can consist of a single sheet, but typically a close coupled pair of sheets is used with the slits of one sheet offset against the slits of the other, so as to minimize the radiation leakage through the curtain.

In a radiation inspection system of the kind just described, the rejection mechanism can be conveniently arranged inside the outfeed compartment and the reject bin can be configured as an expanded lateral portion of the outfeed compartment. By utilizing the space inside the outfeed compartment, this arrangement allows an efficient, space-saving layout with a compact foot print. As mentioned above in the context of the prior art, the layout of the radiation inspection system should be such that the conveyor belt is easily accessible for cleaning as well as easy to uninstall and reinstall for maintenance and replacement. Preferably, the access to the conveyor belt should be from a front side of the radiation inspection system, i.e. the same side where the reject bin is located and is opened for emptying. In particular, it should be possible to take the conveyor belt out of the enclosure cabinet by removing or opening only one enclosure door or enclosure panel on the front side of the radiation inspection system and to pull the belt off its rollers in a frontward direction.

However, the arrangement of the reject bin on the front side, which is also the preferred access side for cleaning, servicing and exchanging the conveyor belt, represents a serious obstacle to the realization of the foregoing layout concept. The reject bin normally restricts the ability to remove and replace the belt due to fixed physical obstructions which are in the belt removal path and which are typically needed to comply with regulatory limits for radiation leakage and to meet the requirements of safe mechanical machine design. Consequently, the belt removal according to current methods is either accomplished from the opposite side of the reject bin assembly, or the reject bin assembly must be electrically and mechanically disconnected and removed to accomplish the task. The latter method requires the physical removal of all or portions of the bin which, in turn, causes machine down-time and loss of productivity.

The object of the present invention is therefore to provide an in-line radiation inspection system of the foregoing description, wherein the conveyor belt can be accessed for cleaning, servicing and belt exchange from the same side of the machine where the reject bin is located, and wherein the conveyor belt can be removed from the enclosure cabinet without having to dismantle all or part of the reject bin.

SUMMARY

This task is solved by an in-line radiation inspection system according to the appended independent claims. Advantageous embodiments and detail features of the invention are set forth in the dependent claims.

An in-line radiation inspection system includes a support structure and an enclosure cabinet, wherein the latter has an infeed opening and an outfeed opening. The enclosure cabinet is internally subdivided into an infeed compartment, an inspection compartment and an outfeed compartment. A conveyor belt runs in a closed loop around rollers that are supported by a conveyor bed and are held under tension by a tensioning mechanism. A transport section of the loop serves to transport inspection objects along a transport path through the infeed compartment, the inspection compartment, and the outfeed compartment. A return section of the loop extends below the transport section back to the infeed compartment. A rejection mechanism is arranged in the outfeed compartment and serves to move rejected objects from the conveyor belt into a reject bin which is configured as an expanded portion of the outfeed compartment extending laterally to one side of the conveyor path. The enclosure cabinet has at least one conveyor access opening with at least one securely closable conveyor access door to allow access for cleaning, servicing and exchanging the conveyor belt. The enclosure cabinet and the conveyor bed are connected to and supported by the support structure on a rear side of the radiation system which is laterally to one side of the conveyor belt, while the enclosure cabinet and the conveyor bed and are free and unconnected to the support structure on a front side of the radiation system which is on the opposite side of the conveyor belt, allowing unobstructed access from the front side to a space below the conveyor bed.

According to the invention, the reject bin and the conveyor access opening are both arranged on the front side, and the reject bin is divided into a reject bin top and a reject bin bottom which are separated along a separation gap. Further according to the invention, the separation gap is arranged at the level of the transport section of the conveyor belt loop and runs uninterrupted from the outfeed opening to the conveyor access opening which, in turn, runs uninterrupted into the infeed opening so that, after the conveyor access door has been opened and the tensioning mechanism has been released, the conveyor belt can be taken out of the enclosure cabinet by passing the transport section of the conveyor belt loop through the separation gap and the conveyor access opening and passing the return section of the conveyor belt loop around the reject bin bottom.

The foregoing solution meets the stated objective perfectly. As the separation gap runs uninterrupted from the outfeed opening to the conveyor access opening and the latter, in turn, continues uninterrupted to the infeed opening while at the same time the configuration of the support structure provides an unobstructed path out of the space below the conveyor bed and around the reject bin bottom, the conveyor belt can be slipped off the conveyor bed and out to the front side of the enclosure cabinet without having to dismantle all or part of the reject bin nor having to disconnect or uninstall any other parts of the radiation inspection system.

Preferably, the separation gap is designed with a downward slant in the direction away from the conveyor belt. The preferred angle of this slant is of the order of 8 to 10° from horizontal. It was found empirically from tests, that a separation gap with a downward slant effectively eliminates the possibility of any stray radiations escaping through the separation gap to the outside.

The conveyor access door is advantageously configured as a hinged flap with a substantially horizontal hinge axis arranged along a bottom edge of the flap at the level of the transport section of the conveyor belt. The hinge flap is designed to swivel between a closed position, where the hinged flap lies flush against the enclosure cabinet and thereby closes and seals the access opening, and at least one open position where the transport section of the conveyor belt loop can be slipped through the uninterrupted passage extending along the separation gap and the conveyor access opening.

In a preferred embodiment, the hinge is configured as a torque hinge that is capable of holding the conveyor access door fixed at any desired swivel angle. In addition, the conveyor access door may be equipped with a snap detent device that locks the conveyor access door in a first open position approximately parallel to the separation gap.

Preferably, the conveyor access door can be swivelled beyond the first open position to a second open position hanging essentially vertically downward from the hinge. This second open position is convenient for cleaning and generally for close access to the interior of the enclosure cabinet, for example to extricate articles that may have become jammed in the rejection mechanism.

In preferred embodiments of the invention, an X-ray generator is arranged in the inspection compartment above the conveyor belt and an X-ray sensor is arranged below the conveyor belt. The conveyor access door can be electrically interlocked with the X-ray generator, whereby power to the X-ray generator is cut off when the conveyor access door is not in its closed position. Persons attending to the radiation inspection system are thus automatically protected against harmful exposure to radiation.

The reject bin bottom is preferably attached to the cabinet or to the conveyor bed by a releasable connection which is electrically interlocked with the X-ray generator, whereby power to the X-ray generator is cut off when the reject bin bottom is removed, for example in order to empty the reject bin bottom of rejected articles. Analogous to the electrical interlock on the conveyor access door, the interlock of the reject bin bottom is likewise a protective measure against harmful exposure to radiation. Alternatively, the reject bin bottom could have a frontal access door or a drawer electrically interlocked with the X-ray generator.

In preferred embodiments of the inventive radiation inspection system, all major components, including the enclosure cabinet, the support structure, the conveyor bed and the reject bin, are equally adapted to being assembled either into a radiation inspection system where the inspection objects move, relative to a frontal view, from left to right, or into a radiation inspection system where the articles move from right to left.

The rejection mechanism in preferred embodiments of the invention can be, for example, a translatory pusher mechanism with a push ram, a sweeper mechanism with a sweeper flap pivoting on an overhead axle, an air blaster to blow a rejected article off the conveyor belt and into the reject bin, or a deflector switch flap that is moved into the transport path to redirect an arriving article to the reject bin.

Advantageously, the reject bin bottom is equipped with an overfill warning sensor with a light emitter/sensor located near a rim of the reject bin bottom and with a light reflector located at a diametrically opposite position of the reject bin bottom. When the rejected articles are piled up high enough in the reject bin bottom, the light beam remains broken, which causes an overfill warning sensor to generate an overfill warning signal.

Additionally, the overfill warning sensor can also be employed as a reject verification sensor. A rejected article falling into the reject bin bottom causes a transient break in the light beam, which causes the overfill warning sensor to generate a reject verification signal. The absence of a verification signal subsequent to an activation of the rejection mechanism could indicate a malfunction such as jamming of the rejection mechanism.

The radiation inspection system described herein is advantageously designed as an X-ray inspection system. Of course, the inspection system presented here is not limited to X-ray radiation but also could be used with other radiation generators of different wavelength.

BRIEF DESCRIPTION OF THE DRAWINGS

The in-line radiation inspection system according to the invention will be described hereinafter through embodiments shown schematically in the drawings, wherein.

DETAILED DESCRIPTION OF THE EMBODIMENTS

Figure 1:
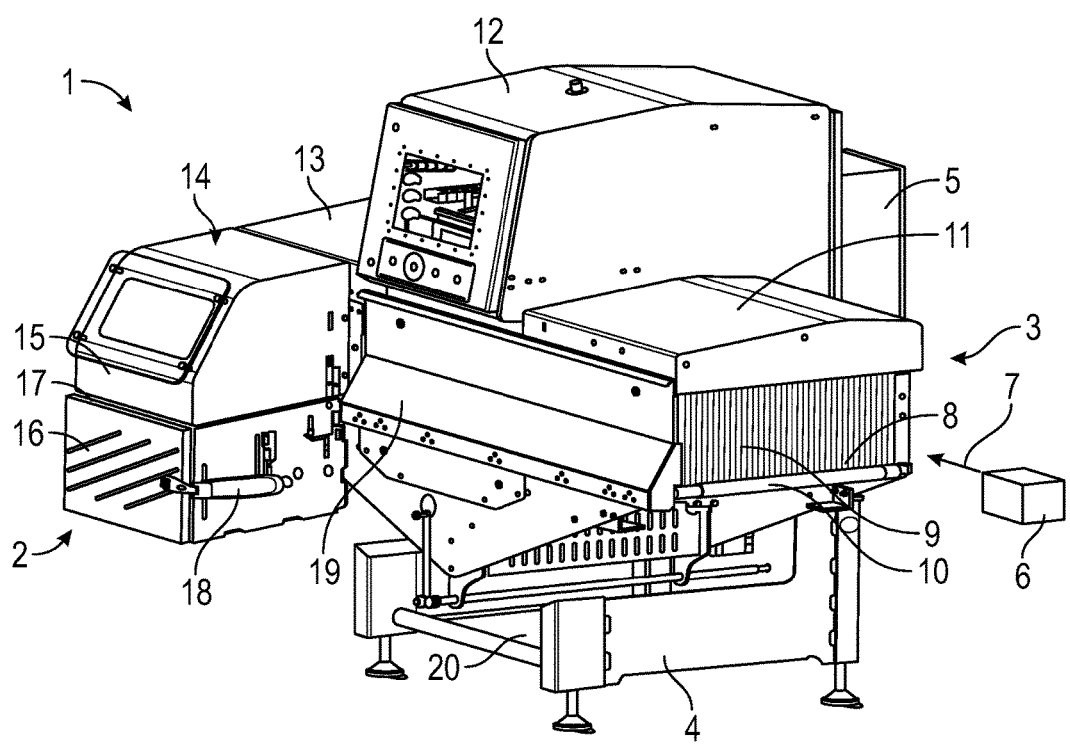
FIG. 1 illustrates the in-line X-ray system of the invention in a perspective view with the conveyor access door closed.

An in-line X-ray system 1 according to the invention is shown in FIG. 1 to provide a general overview of the system parts and their respective functions. For reference within the present context, a front side and a rear side of the in-line X-ray system 1 are defined, respectively, by arrows 2 and 3. The in-line X-ray system 1 includes a support structure 4 and an enclosure cabinet 5. An article 6 that is to be inspected enters the in-line X-ray inspection system 1 in the direction indicated by the arrow 7, passing through the infeed opening 8 with the first radiation-shielding curtain 9. Inside the enclosure cabinet 5, the article 6 is transported on a conveyor belt 10 which can be seen below the first shielding curtain 9. The general layout of the enclosure cabinet is divided into an infeed compartment 11, an inspection compartment 12 containing the X-ray generator in its prominent top portion, an outfeed compartment 13, and a reject bin 14 arranged on the front side of the outfeed compartment 13. The reject bin 14 is split into a reject bin top 15 and a reject bin bottom 16 along the separation gap 17. A locking device 18 secures the reject bin bottom 16 and automatically cuts power to the X-ray generator 36 (see FIG. 2) when the reject bin bottom 16 is taken off for emptying. The conveyor access door 19—shown here in its closed position—extends in this view to the right of the reject bin 14 over the entire remaining width of the front side of the enclosure cabinet 4. The enclosure cabinet 5 which encloses all of the functional parts of the in-line X-ray inspection system 1 is connected to and supported by the support structure 4 only on the rear side 3 of the in-line X-ray inspection system 1, allowing unobstructed access from the front side to the air space 20 below the enclosure cabinet 5.

Figure 2:
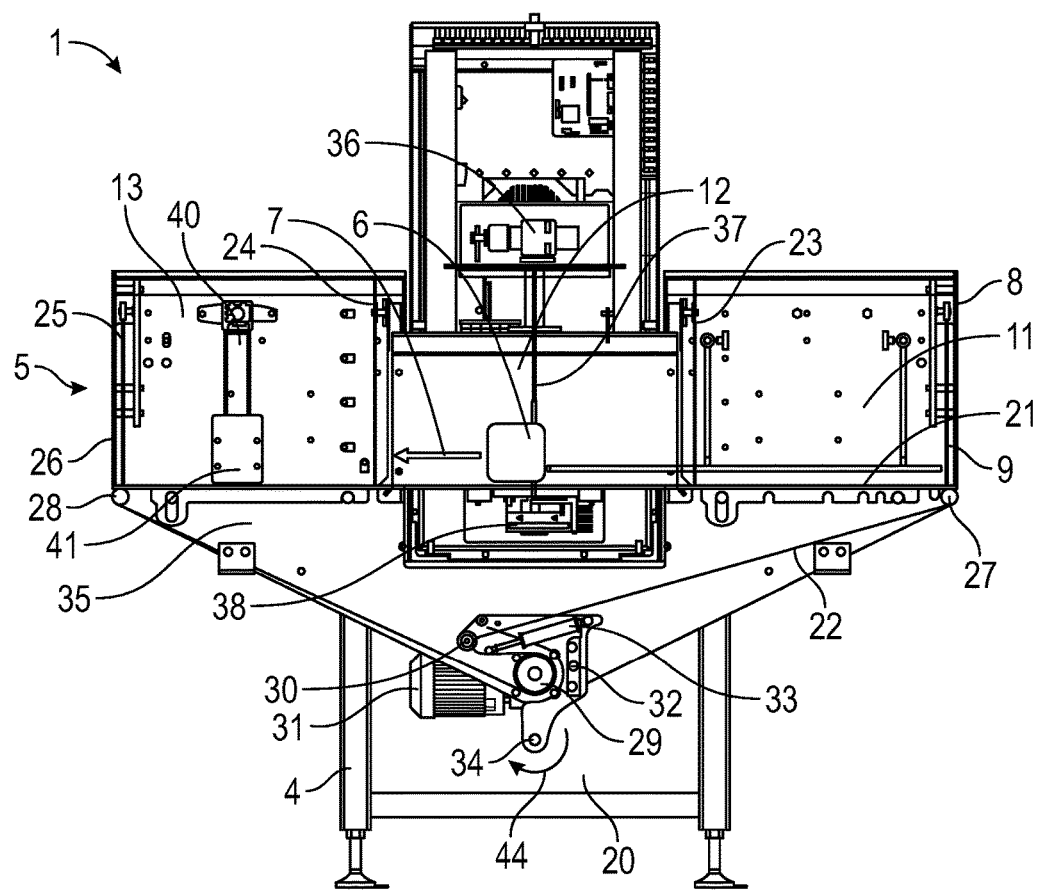
FIG. 2 represents a cross-sectional elevation drawing of the in-line X-ray system of FIG. 1 in a vertical section plane along the center line of the conveyor transport path.

FIG. 2 shows the in-line X-ray system 1 of FIG. 1 in a cross-sectional elevation drawing in a vertical section plane along the center line of the conveyor transport path. The transport direction for an inspection object 6 in this view runs right to left, as indicated by the arrow 7. Entering through the first radiation-shielding curtain 9 at the infeed opening 8, inspection objects 6 are carried by the horizontal transport section 21 of the conveyor belt 10 through the infeed compartment 11, the second radiation-shielding curtain 23, the inspection compartment 12, the third radiation-shielding curtain 24, the outfeed compartment 13, and the fourth radiation-shielding curtain 25 at the outfeed opening 26. A return section 22 of the loop extends below the transport section 21 back to the infeed opening 8. The conveyor belt 10 runs in a closed loop around end rollers 27, 28, a drive roller 29 which is coupled to a drive motor 31, and a tensioning roller 30. The tensioning roller 30 is part of a tensioning mechanism 32 shown here with a symbolically indicated hydraulic belt tensioner 33. In the illustrated operating state, the tensioning mechanism 32 serves to maintain a specified amount of tension of the conveyor belt 10. In a released state (not shown here) the tensioning mechanism 32 is rotated in the direction of the circular arrow 44 about the swivel axis 34 into a belt-release position where the conveyor belt 10 is in a totally slack condition for belt removal or exchange. The belt rollers 27, 28, 29, 30, the drive motor 31 and the tensioning mechanism 32 are supported by the conveyor bed 35, i.e. the triangular assembly extending downward of the horizontal transport section 21 of the conveyor belt 10. The X-ray generator 36 is arranged in the inspection compartment 12 above the horizontal transport section 21 of the conveyor belt 10, emitting X-rays in a fan-shaped laminar beam 37 (appearing only as a vertical line in this view) which traverses the inspection object 6 and the transport section 21 of the conveyor belt 10 and is received by an X-ray sensor 38 which is arranged below the horizontal transport section 21 of the conveyor belt 10. A rejection mechanism 40 with a pusher 41 is arranged in the outfeed compartment 13 and serves to move rejected objects from the transport section 21 of the conveyor belt into the reject bin 14 (see FIG. 1).

Figure 3:
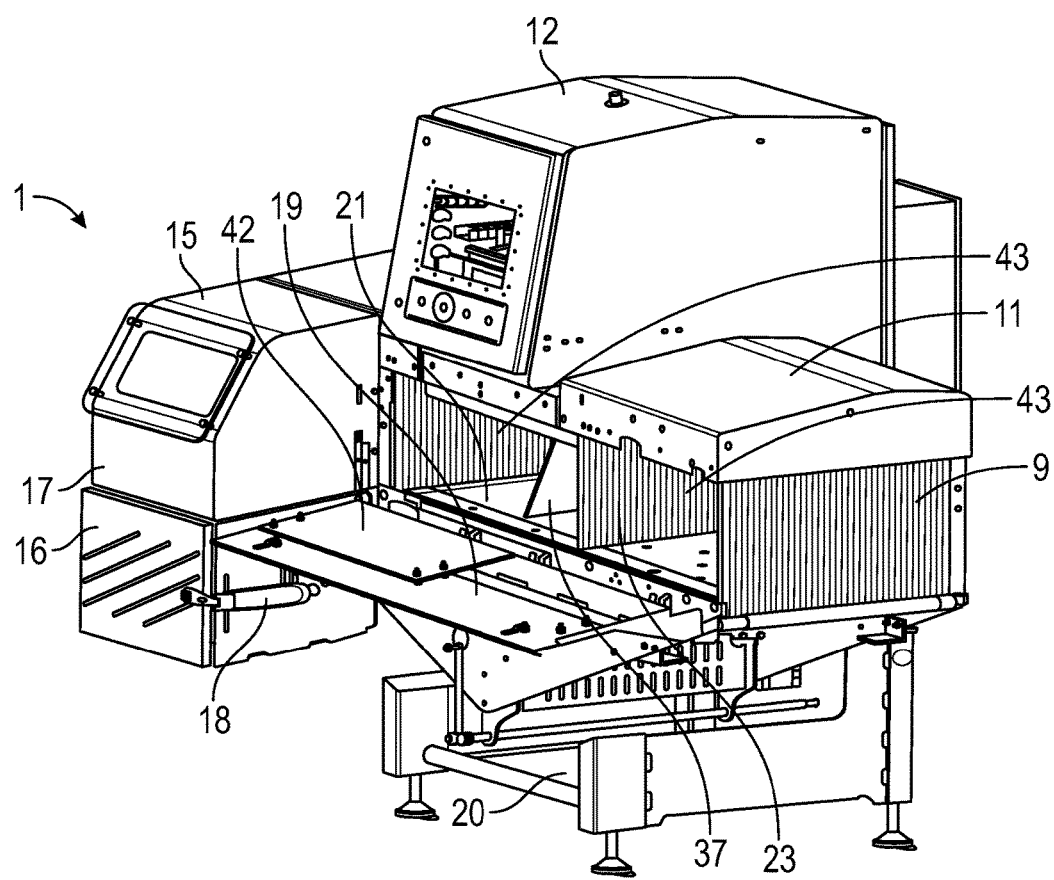
FIG. 3 illustrates the in-line X-ray system of FIG. 1 with the conveyor access door lowered to a first open position for removal/exchange of the conveyor belt.

FIG. 3 shows the in-line X-ray inspection system 1 with the conveyor access door 19 in the first open position, so that the interior of the infeed compartment 11 and the inspection compartment 12 can be seen through the conveyor access opening 43. The drawing provides a perspective view of most of the elements that have already been shown in FIGS. 1 and 2 with the same reference symbols and are therefore not explained again. The additional radiation shield 42 which is overlaid on the inside of the conveyor access door 19 provides an additional radiation barrier on the front side of the inspection compartment 12. The separation gap 17 is inclined at a downward slant—about 8 to 10° from horizontal—in the direction away from the conveyor belt 10. As mentioned previously herein, a separation gap 17 with a downward slant effectively eliminates the possibility of any stray X-rays escaping through the separation gap 17 to the outside. On the outfeed side of the X-ray system 1 (facing away from the viewer and not visible in the drawing) and on the near side, i.e. towards the conveyor access door 19, the separation gap 17 is open towards the front side edge of the horizontal transport section 21 of the conveyor belt 10. Thus, with the conveyor access door 19 open, and after the tensioning mechanism 32 has been released, the conveyor belt 10 can be taken out of the enclosure cabinet 5 by passing the transport section 21 of the conveyor belt 10 through the separation gap 17 and through the access opening 43 and by passing the slack return section 22 of the conveyor belt loop 10 out of the air space 20 and around the reject bin bottom 16.

What is claimed is:

1. A system for inspecting inspection objects using radiation, comprising:
    a support structure;
    an enclosure cabinet, comprising:
        an infeed opening; and
        an outfeed opening;
        an interior of the enclosure cabinet subdivided into an infeed compartment,
    an inspection compartment and an outfeed compartment;
    a conveyor bed that supports rollers and a tensioning mechanism;
    a conveyor belt that runs in a closed loop around the rollers while being held under tensioning by the tensioning mechanism, defining a conveyor belt loop that is divided into a transport section that transports the inspection objects along a transport path through the infeed compartment, the inspection compartment, and the outfeed compartment and a return section that runs below the transport section from the outfeed opening back to the infeed opening, wherein, to allow access for cleaning, servicing and exchanging the conveyor belt, the enclosure cabinet has at least one conveyor access opening with a conveyor access door;
    a reject bin, configured as an expanded portion of the outfeed compartment that protrudes sideways from the enclosure cabinet laterally to one side of the conveyor belt, the reject bin being divided into a reject bin top and a reject bin bottom which are separated along a separation gap from each other, the separation gap being arranged at the level of the transport section of the conveyor belt loop to run uninterrupted from the outfeed opening to the conveyor access opening, which, in turn, runs uninterrupted into the infeed opening so that, after the conveyor access door has been opened and the tensioning mechanism has been released, the conveyor belt can be taken out of the enclosure cabinet by sliding the transport section of the conveyor belt loop out to the front through the separation gap and the conveyor access opening, and by slipping the return section of the conveyor belt loop around the reject bin bottom; and
    a rejection mechanism, arranged in the outfeed compartment, to move inspection objects that are rejected from the conveyor belt into the reject bin;
    wherein the enclosure cabinet and the conveyor bed are connected to and supported by the support structure on a rear side thereof which is laterally to one side of the conveyor belt, while the enclosure cabinet and the conveyor bed are clear of the support structure on a front side thereof, which is on the opposite side of the conveyor belt and the reject bin and the conveyor access opening are both arranged on the front side.

2. The system of claim 1, wherein the separation gap has a downward slant in the direction away from the transport section of the conveyor belt.

3. The system of claim 2, wherein the downward slant has an angle that is of the order of 8 degrees to 10 degrees from horizontal.

4. The system of claim 1, wherein:
    the conveyor access door is configured as a hinged flap with a substantially horizontal hinge axis arranged along a bottom edge of the flap at the level of the transport section of the conveyor belt, and
    the hinged flap is designed to swivel between a closed position, where the hinged flap lies flush against the enclosure cabinet, closing and sealing the access opening, and at least one open position where the transport section of the conveyor belt loop can be slipped out to the front through the separation gap and the conveyor access opening.

5. The system of claim 4, wherein the hinge of the conveyor access door is configured as a torque hinge that can hold the conveyor access door fixed at any desired swivel angle.

6. The system of claim 4, wherein the conveyor access door further comprises a snap detent device that locks the conveyor access door in a first open position approximately parallel to the separation gap.

7. The system of claim 6, wherein the conveyor access door can be swivelled beyond the first open position to a second open position hanging essentially vertically downward from the hinge.

8. The system of claim 2, wherein:
    the conveyor access door is configured as a hinged flap with a substantially horizontal hinge axis arranged along a bottom edge of the flap at the level of the transport section of the conveyor belt, and
    the hinged flap is designed to swivel between a closed position, where the hinged flap lies flush against the enclosure cabinet, closing and sealing the access opening, and at least one open position where the transport section of the conveyor belt loop can be slipped out to the front through the separation gap and the conveyor access opening.

9. The system of claim 8, wherein the hinge of the conveyor access door is configured as a torque hinge that can hold the conveyor access door fixed at any desired swivel angle.

10. The system of claim 8, wherein the conveyor access door further comprises a snap detent device that locks the conveyor access door in a first open position approximately parallel to the separation gap.

11. The system of claim 1, wherein subassemblies and components of the system are equally adapted to being assembled for inspection objects move, relative to a frontal view, either from left to right or from right to left.

12. The system of claim 1, wherein the rejection mechanism is one of:
    a translatory pusher mechanism with a push ram;
    a sweeper mechanism with a sweeper flap pivoting on an overhead axle;
    an air blaster to blow a rejected inspection object off the conveyor belt and into the reject bin, or
    a deflector switch flap that is moved into the transport path to redirect an arriving inspection article to the reject bin.

13. The system of claim 1, wherein the reject bin bottom has an overfill warning sensor comprising a light emitter, located inside the reject bin bottom near the separation gap; and a light reflector, located at a diametrically opposite position of the reject bin bottom, such that when the rejected inspection objects pile up high enough in the reject bin bottom, a light beam emitted by the light emitter and reflected by the light reflector remains broken, which causes the overfill warning sensor to generate an overfill warning signal.

14. The system of claim 13, wherein the overfill warning sensor is additionally employed as a reject verification sensor, wherein a transient break in the light beam due to a rejected inspection object falling into the reject bin bottom causes the overfill warning sensor to generate a reject verification signal, and the absence of a verification signal or an overfill signal subsequent to an activation of the rejection mechanism indicates a malfunction of the rejection mechanism or a failure of the warning sensor.

15. The system of claim 1, further comprising:
   an X-ray generator, arranged in the inspection compartment above the transport section of the conveyor belt; and
   an X-ray sensor, arranged below the transport section of the conveyor belt.

16. The system of claim 15, wherein the conveyor access door is electrically interlocked with the X-ray generator, such that power to the X-ray generator is cut off when the conveyor access door is not in its closed position.

17. The system of claim 15, wherein the reject bin bottom is attached to the enclosure cabinet or to the conveyor bed by a releasable locking device which is electrically interlocked with the X-ray generator, such that power to the X-ray generator is cut off when the reject bin bottom is removed.

18. The system of claim 15, wherein the reject bin bottom has a frontal access door or a drawer that is electrically interlocked with the X-ray generator.

* * * * *